(12) United States Patent
Antaki et al.

(10) Patent No.: US 6,270,472 B1
(45) Date of Patent: Aug. 7, 2001

(54) APPARATUS AND A METHOD FOR AUTOMATICALLY INTRODUCING IMPLANTS INTO SOFT TISSUE WITH ADJUSTABLE SPACING

(75) Inventors: James F. Antaki, Allison Park; Joel S. Greenberger, Sewickley; John A. Holmes; Philip Schauer, both of Wexford, all of PA (US)

(73) Assignee: University of Pittsburgh of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 09/222,172

(22) Filed: Dec. 29, 1998

(51) Int. Cl.$^7$ .......................... A61M 31/00; A61M 36/00
(52) U.S. Cl. .................... 604/61; 604/60; 600/7
(58) Field of Search .................. 604/57, 59–64, 604/502, 506, 93.01, 224; 600/3, 7, 8

(56) References Cited

U.S. PATENT DOCUMENTS

| 2,761,446 | 9/1956 | Reed . | |
|---|---|---|---|
| 3,921,632 | 11/1975 | Bardani | 128/217 |
| 4,086,914 | 5/1978 | Moore | 128/1.2 |
| 4,167,179 | 9/1979 | Kirsch | 128/1.2 |
| 4,402,308 | 9/1983 | Scott | 128/1.2 |
| 4,461,280 | 7/1984 | Baumgartner | 128/1.2 |
| 4,597,753 | 7/1986 | Turley . | |
| 4,700,692 | 10/1987 | Baumgartner | 128/1.2 |
| 4,763,642 | 8/1988 | Horowitz | 128/1.2 |
| 4,815,449 | 3/1989 | Horowitz . | |
| 4,994,028 | 2/1991 | Leonard et al. . | |
| 5,242,373 | 9/1993 | Scott et al. | 600/7 |
| 5,250,026 | 10/1993 | Ehrlich et al. . | |
| 5,281,197 | * 1/1994 | Arias et al. | 604/57 |
| 5,324,306 | * 6/1994 | Makower et al. | 606/213 |
| 5,562,613 | 10/1996 | Kaldany | 604/57 |
| 5,676,681 | 10/1997 | Yoon . | |
| 5,938,583 | * 8/1999 | Grimm | 600/7 |
| 6,007,474 | * 12/1999 | Rydell | 600/7 |
| 6,102,844 | * 8/2000 | Ravins et al. | 600/8 |

FOREIGN PATENT DOCUMENTS 0 584 959 A2   3/1994   (EP) .
0 639 387 A1   2/1995   (EP) .

* cited by examiner

Primary Examiner—Sharon Kennedy
(74) Attorney, Agent, or Firm—Richard V. Westerhoff; Eckert Seamans Cherin & Mellott, LLC

(57) ABSTRACT

Apparatus and a method for depositing multiple implants carrying radioactive isotopes, pharmalogical agents or transgenes, in soft tissue including tumors and organs with precise, selectable spacing between implants includes an introducer in the form of a tube which is inserted into the soft tissue and an obturator for pushing implants out of the introducer one at a time. An operating mechanism incrementally withdraws the introducer while the obturator remains stationary thereby depositing a single implant. The obturator is then coupled to the introducer for the remainder of the stroke to provide the spacing. In a preferred embodiment, the introducer is resequenced to lay down parallel rows of implants. An indicator records the total number of implants deposited. The distal end of the introducer is configured to retain the implants and allow them to be discharged into the soft tissue singly. The invention is particularly suited, but not limited, to depositing the implants using laporascopic or thorascopic techniques.

56 Claims, 10 Drawing Sheets

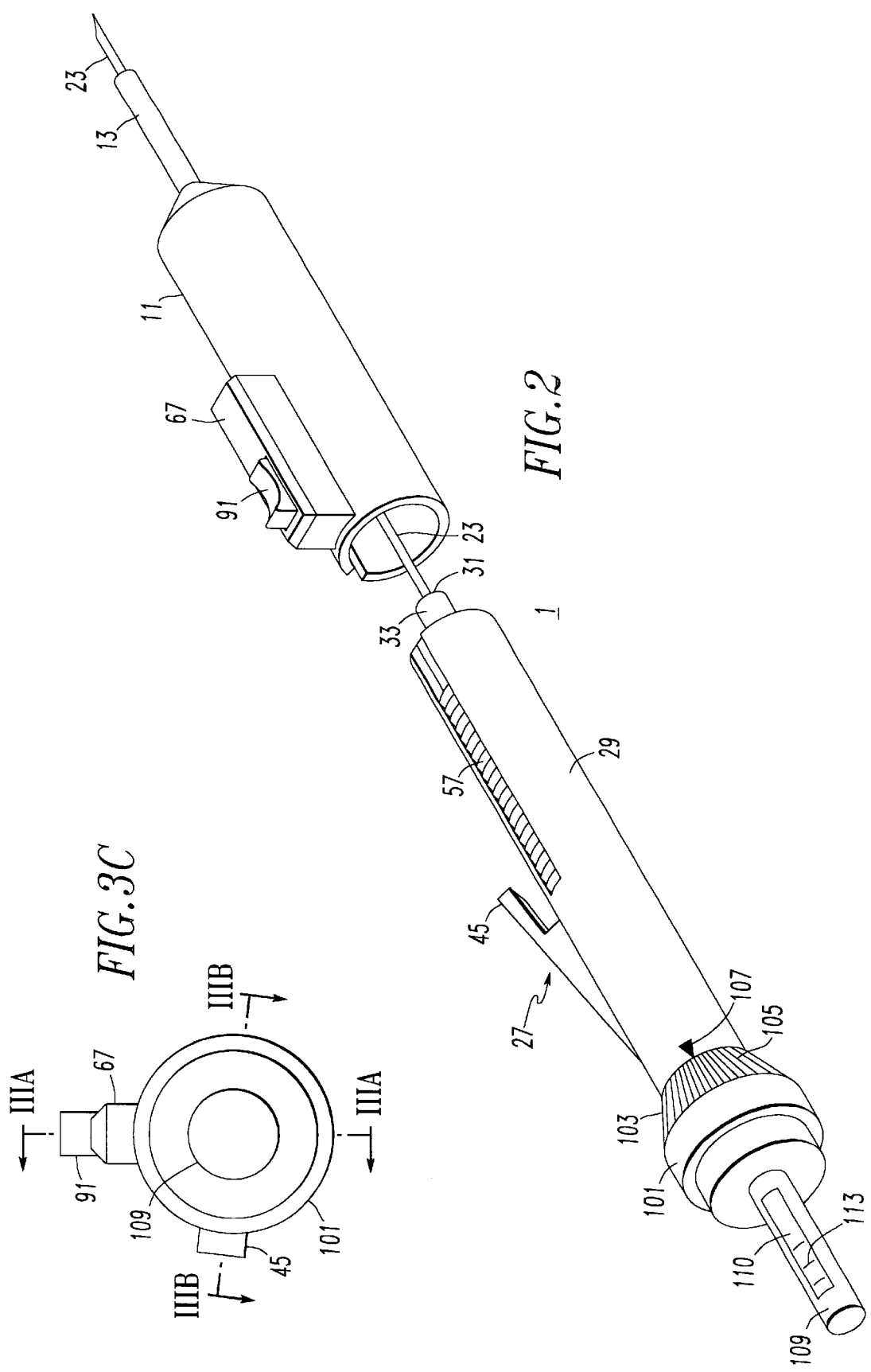

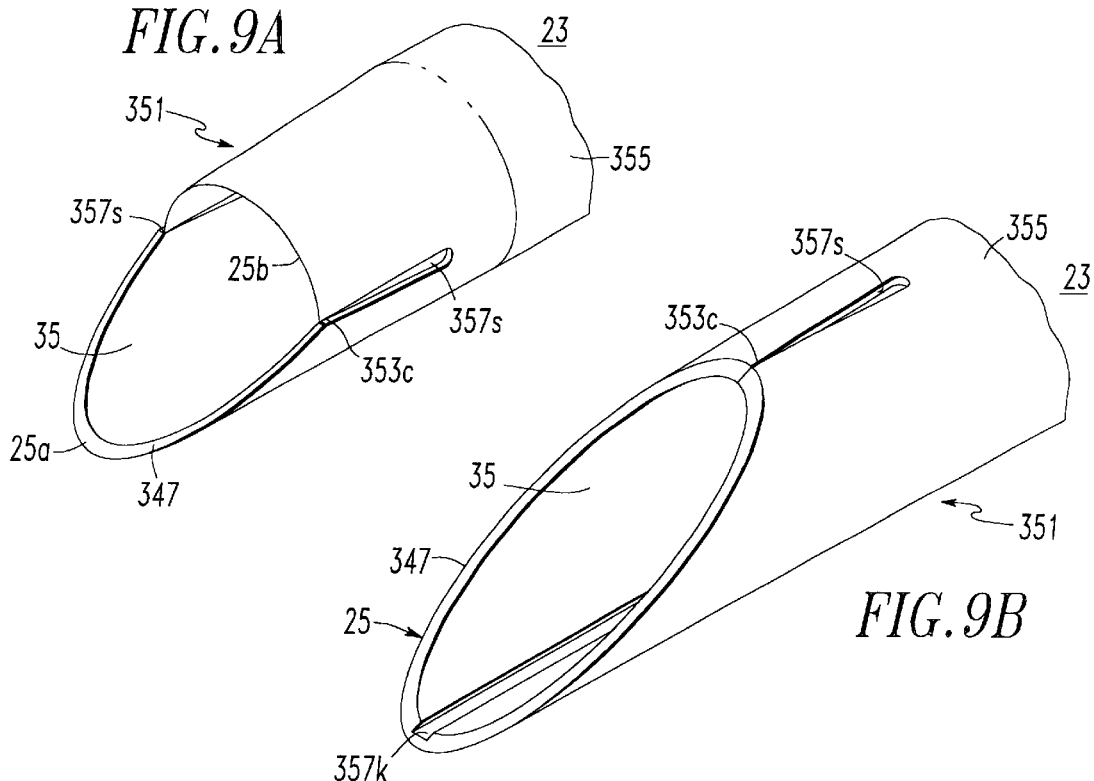
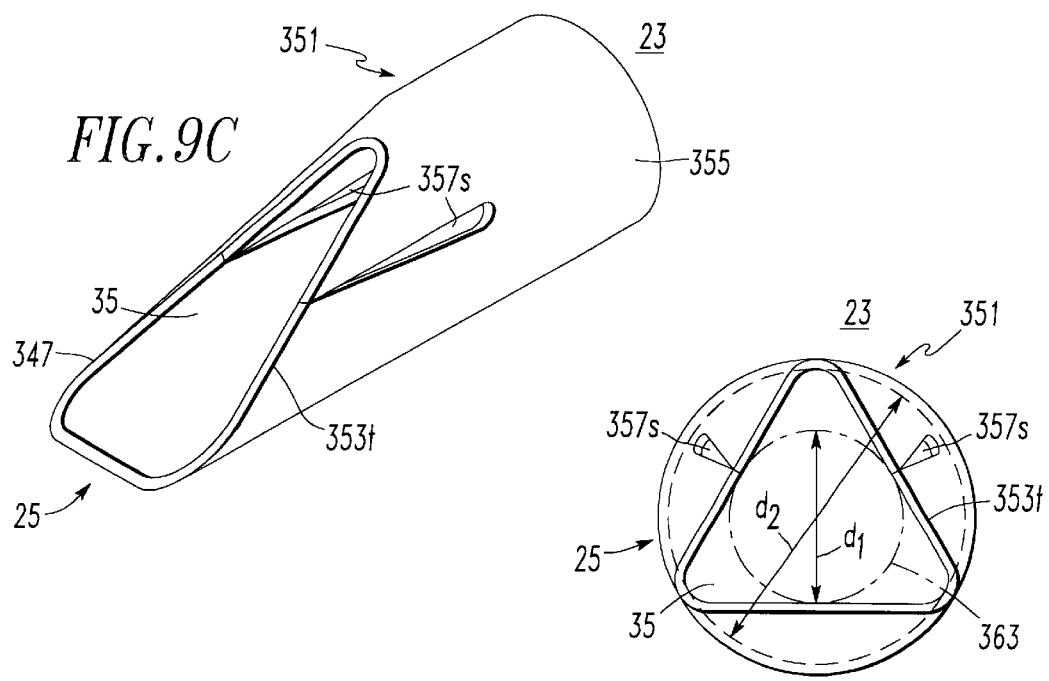

APPARATUS AND A METHOD FOR AUTOMATICALLY INTRODUCING IMPLANTS INTO SOFT TISSUE WITH ADJUSTABLE SPACING

BACKGROUND OF THE INVENTION

1. Field of the Invention

This invention relates to apparatus and a method for introducing implants such as radioactive seeds, or pellets or dissolvable capsules carrying medication or transgenes, into soft tissue such as tumors, and particularly intra-abdominal or intrathoracic tumors. Specifically, it relates to such an apparatus and method which deposits multiple implants in soft tissue with precise, selectable spacing between implants.

2. Background Information

It is known to inject radioactive seeds into the prostate to treat malignancies. Early devices for this purpose injected a single seed using a hollow needle from which the seed was ejected by a plunger. Later devices have the capability of introducing multiple seeds. Some deposit a single elongated implant having multiple seeds distributed longitudinally. Others have a plunger with multiple, axially spaced seed cavities inserted through a cannula with equally spaced side openings for laterally discharging the seeds. Neither of these approaches offer flexibility in the spacing between multiple implants. Furthermore, there is difficulty in laterally discharging the implants in the second arrangement. It has been proposed to incorporate small leaf springs in the cavities to push the implants clear of the cannula, but withdrawing the cannula past the seeds disturbs their positions and the diameter of the cannula must be enlarged to accommodate the springs. Still other multiple seed ejectors rely upon the user to set the spacing between seeds. The accuracy of this technique is dependent upon the skill of the user or requires fluoroscopy to monitor seed location.

There is a need for an improved apparatus for introducing implants into soft tissue.

There is a particular need for an improved apparatus for introducing multiple implants at precisely spaced locations within the soft tissue.

There is a related need for such apparatus with which the spacing between implants can be easily and accurately adjusted.

There is also a need for such apparatus which can be used to introduce implants into soft tissue within a cavity such as intra-abdominal and intrathoracic tumors.

There is an additional need for such apparatus which can be easily loaded and simple to use, and particularly which only requires one hand of the user to deposit the implants with precise spacing.

There is a further need for such a device which can be used for various types of implants, such as radioactive seeds, or pellets bearing or dissolvable capsules containing medications or transgenes.

SUMMARY OF THE INVENTION

These needs and others are satisfied by the invention which is directed to apparatus and a method for introducing implants into soft tissue at spaced intervals.

The apparatus includes an introducer in the form of an elongated tube having a distal end which is insertable into the soft tissue and within which a plurality of implants are retained. An obturator is slidable within the introducer from the proximal end. The apparatus further includes a sleeve through which the introducer slidably extends. An operating means incrementally withdraws the introducer rearward relative to the sleeve a distance L. Initially, the obturator remains stationary while the introducer is withdrawn so that an implant is pushed out of the end of the introducer. After the introducer has been withdrawn a distance $L_s$ equal to the length of one implant, automatic coupling means of the operating mechanism couples the obturator to the introducer so that both the obturator and the introducer are withdrawn the remainder of the distance L. This distance $L_p$ that the obturator and introducer are withdrawn together provides spacing between the implants. Thus, the implants are deposited within the soft tissue with precise spacing in between. In accordance with one aspect of the invention, this spacing $L_p$ is adjustable.

The implants which are deposited by the apparatus of the invention can be radioactive seeds. They can also be dissolvable capsules containing medication or transgenes. The implants can also be resorbable pellets carrying medication or transgenes. The invention is particularly suitable for depositing implants in intra-abdominal and intrathoracic tumors. In such case, the sleeve of the apparatus can have a tubular extension which is inserted through an incision in the external wall defining the cavity in which the tumor is located. The tubular extension can be positioned for inserting the introducer into the tumor by a laparoscope or thoracoscope inserted through another small incision as is known. This eliminates the need to use a fluoroscope or an open incision to align the apparatus with a tumor. With the tubular extension on the sleeve properly aligned relative to the tumor, the introducer is extended through the tubular extension into the tumor. To this end, the introducer is provided with a sharpened end.

Several lines of spaced implants can be deposited within the tumor using the invention. After each line of implants has been deposited, the tubular extension is repositioned such as by using the laparoscope or thoracoscope and the procedure is repeated. As used throughout, the term "forward" will be used in reference to movement toward or into the soft tissue and the term "rearward" in reference to movement away from or out of the soft tissue.

The preferred embodiment of the invention is particularly suited for depositing multiple lines of implants in soft tissue. In this embodiment, the introducer has an enlarged proximal end in the form of a tubular member which is received in the sleeve. The means incrementally withdrawing the introducer comprises a trigger mechanism including a trigger supported on the tubular member. A slide is slidable forward relative to the tubular member upon actuation of the trigger. A one-way clutch locks the slide to the sleeve as the trigger is actuated so that, in effect, the slide remains stationary relative to the sleeve and the tubular member is incrementally withdrawn rearward the distance L with respect to the sleeve each time the trigger is actuated. The means automatically coupling the obturator to the introducer is a holding device engaged by the slide which holds the obturator stationary relative to the sleeve until the introducer has been withdrawn the distance $L_s$. A slip clutch through which the obturator slips as the introducer moves the distance $L_s$ couples the obturator to the introducer for movement with the introducer over the distance $L_p$.

Preferably, the one-way clutch which locks the slide to the sleeve includes a rack and a pawl member, with the rack provided on the slide and the pawl member mounted on the sleeve. A spring biases the slide rearward upon release of the trigger. Means such as an O-ring resist forward movement of the tubular member relative to the sleeve in response to this bias. As the slide moves rearward, the pawl member slides over the rack teeth and the apparatus is ready for deposit of another implant by reactuation of the trigger. Each time the trigger is actuated, the tubular member, and therefore the introducer, moves incrementally rearward to deposit an implant and provide the spacing $L_p$. When the desired number of implants have been deposited in a row, the pawl member is lifted, and the tubular member/introducer is slid forward relative to the sleeve to reset the introducer for laying down another row of implants.

In the preferred embodiment of the invention, the means holding the obturator stationary relative to the sleeve while the implant is deposited comprises a fore shuttle slidable in the tubular member, and a directional clutch blocking rearward movement of the obturator relative to the fore shuttle. This holding device further includes a decoupling spring between the slide and the fore shuttle holding the fore shuttle stationary relative to the sleeve while the introducer moves the distance $L_s$ relative to the sleeve until the fore shuttle seats relative to the tubular member and is then carried rearward with the tubular member against the decoupling spring to provide the spacing $L_p$ between implants. A return spring between the fore shuttle and the tubular member biases the fore shuttle away from seating relative to the tubular member and repositions it upon release of the trigger. The decoupling spring is stronger than the return spring so that initially the shuttle, and therefore the obturator, remains stationary relative to the slide, and the sleeve, while the introducer is withdrawn the distance $L_s$.

In the above-described preferred embodiment of the apparatus, the means for adjusting the spacing $L_p$ is in the form of a tubular adjusting member threaded onto the inner end of the tubular member forming an adjustable stop which limits the travel of the slide, preferably through engagement with the trigger. The preferred embodiment of the invention can be used without the sleeve. In such case, an implant is ejected from the introducer with each actuation of the trigger. The introducer must be manually retracted by the user to provide spacing between implants.

In another embodiment of the invention the means for incrementally withdrawing the introducer relative to the sleeve comprises a carriage slidable within the sleeve. It firer includes means reciprocating the carriage forward and rearward within the sleeve and means coupling the introducer to the carriage only as the carriage moves rearward. The means coupling the obturator to the introducer in this embodiment of the invention comprises a shuttle slidable in the housing and means positioning the shuttle for engagement by and movement rearward with the carriage after the introducer has been moved inward by the distance $L_s$. The means positioning the shuttle for engagement by the carriage comprises a bias means such as a spring biasing the shuttle toward the carriage and a first stop against which the shuttle seats to set the distance $L_s$ at which the shuttle is engaged by the carriage.

The means reciprocating the carriage within the sleeve in this second embodiment of the invention is a trigger assembly and a trigger coupling linking the trigger assembly to the carriage. The trigger assembly includes a trigger member mounted for rectilinear movement generally transverse to the introducer. The trigger coupling includes a coupling pin on either the trigger member or the carriage and a coupling slot in the other of the trigger member and the carriage oriented at an angle to both the rectilinear movement of the trigger member and the forward and rearward movement of the carriage and engaged by the coupling pin. A second bias means in the form of another spring biases the carriage forward. In this embodiment of the invention, the arrangement for adjusting the distance $L_p$ between implants can be a device such as an adjustment screw setting the length $L_r$ of the rectilinear movement of the trigger member. Alternatively, the same arrangement as described in connection with the preferred embodiment can be used to adjust the spacing $L_p$ in this second embodiment.

In yet another embodiment of the invention, the means for repetitively, incrementally withdrawing the introducer relative to the sleeve is a walking mechanism which incrementally walks rearward in the sleeve the distance L. This walking mechanism comprises a first actuating member secured to the introducer adjacent the proximal end thereof. It further includes a glide slidable in the sleeve rearward of the introducer and a second actuating member secured to the glide. First and second clutch means restrain forward movement of the introducer and the glide respectively. A spring biases the introducer and glide apart. The first and second actuator members are positioned for movement toward each other in response to an external actuating force. As the second clutch means holds the glide against forward movement, the introducer is drawn rearward. The actuating members are separated by the spring upon release of the external force. As the first clutch means holds the introducer against forward movement, the glide is pushed rearward to complete the walking motion. In this embodiment, the means automatically coupling the obturator to the introducer is a shuttle slidable relative to the glide between the introducer and the glide. The shuttle is engaged by and moved rearward with the introducer after the introducer has moved rearward the distance $L_s$. Means on the shuttle grip the obturator for rearward movement with the shuttle. The glide is provided with a shuttle stop limiting forward movement of the shuttle relative to the glide. A second spring biases the shuttle against the shuttle stop. A third clutch means restrains rearward movement of the obturator relative to the introducer. A fourth clutch means restrains rearward movement of the obturator with the introducer until the shuttle is engaged by the introducer. An adjustment means limits movement of the actuating members toward each other to adjust the spacing between implants.

As another aspect of the invention, restraining means are incorporated into the distal end of the introducer to prevent implants from falling out. This integral restraining means reduces the passage in the introducer at the distal end to an inscribed opening which is smaller in lateral dimension than that of the implants, yet is resiliently expandable for ejection of implants by the obturator. The restraining means comprises radially inwardly directed deformations and strain relief cuts in the introducer. The deformations may be in the form of a crimp or dimples. The cuts are either slits extending through the introducer wall or kerfs extending only partially through the wall. Preferably, these slits or kerfs are longitudinal, and they may be open ended, in that they extend to the distal end of the introducer, or they may be closed, stopping short of the distal end.

As a further aspect of the invention, a gauge provides an indication of the number of implants which have been deposited. This gauge is provided by a tubular housing mounted on the rear of the device into which the obturator extends. A graticule on a transparent tubular housing or a window in the housing provides a visual indication of the position of the obturator, and therefore, the number of implants deposited. Where adjustment of the spacing is provided by the tubular adjustment collar on the rearward end of the sleeve, and the tubular obturator housing is integral with this adjustment collar, a helical scribe line is provided on the obturator for cooperating for the graticule to maintain accuracy of the implant count with adjustment of the spacing $L_p$.

A depth or penetration gauge can also be provided by a scale on a fully or partially transparent extension on the sleeve and a mark on the introducer which registers with the scale to indicate the depth of penetration of the introducer into soft tissue.

The invention also embraces a method of introducing a gene into soft tissue. This method includes loading an implant carrying a nucleic acid sequence encoding the gene into an introducer, inserting the introducer into the soft tissue, ejecting the implant into the soft tissue from the introducer, and withdrawing the introducer from the soft tissue. The soft tissue can be a tumor in which the gene can be used to suppress the growth of the tumor in serving as an anti-oncogene, anti-growth factor receptor, antisense message for binding of growth factor receptor, or other signal-transducing substances RNA or can stimulate apoptosis. Alternatively, the soft tissue could be an organ such as the liver or pancreas and the gene can provide for the direction of transcripts that reduce toxicity from cancer therapy such as adding antioxidant genes, radiation resistance gene product substances, or can add genes that produce transcripts for antisense endothelial cell or cell surface attachment molecules, thereby preventing metastasis of cancer cells from other sites into that organ such as the pancreas or liver.

The method includes depositing a plurality of implants in the soft tissue by loading them into the introducer and ejecting them from the introducer into the soft tissue one at a time in spaced relation. Preferably, the implants are deposited by inserting an obturator into the introducer behind the implants. The implants are injected by holding the obturator stationary relative to the soft tissue while the introducer is withdrawn. Multiple implants are ejected one at a time in spaced relation as the introducer is withdrawn from the soft tissue. Preferably this is accomplished by, repetitively withdrawing the introducer while holding the obturator stationary to eject an implant and then withdrawing the introducer and the obturator together to provide the spacing between implants. Multiple lines of implants can be deposited in this manner by reinserting the introducer into the soft tissue and laying down an additional line of implants. Where the soft tissue is located within the cavity such as the abdomen or the thorax, laporascopic or thorascopic techniques can be used to align the introducer for insertion into the soft tissue. Thus, the method includes inserting the introducer through an incision in an external wall defining a cavity containing the soft tissue and inserting an optical instrument such as a laparoscope or a thoracoscope into the cavity through another incision to visually align the introducer for depositing one or more rows of implants in the soft tissue.

While the implants are deposited in soft tissue in accordance with the invention by ejecting them from the distal end of the introducer through relative movement of the obturator toward the distal end of the introducer, the implant in fact remains in a fixed position in the soft tissue because the relative motion is produced by withdrawing the introducer while the obturator remains stationary thereby exposing the implant to the surrounding tissue. This provides several advantages. First, it minimizes trauma to the tissue. Second, it prevents an implant placed deeply in the tissue from being advanced beyond the distal margin of the tissue which would necessitate a tedious retrieval of the implant. Third, consistent separation of multiple implants within a single track and the location of the line of implants with respect to the surface of the soft tissue are assured.

BRIEF DESCRIPTION OF THE DRAWINGS

A full understanding of the invention can be gained from the following description of the preferred embodiments when read in conjunction with the accompanying drawings in which:

FIG. 2 is an isometric view of an apparatus in accordance with the preferred embodiment of the invention as shown partially assembled.

FIG. 3C is an end view of the apparatus of FIG. 2 showing the planes of the sections of FIGS. 3A and 3B.

FIGS. 9A–9C, 9E and 9F are isometric views of various embodiments of the distal end of the introducer which forms part of the apparatus of the invention.

FIG. 9D is an end view of the distal end of the introducer shown in FIG. 9C.

DESCRIPTION OF THE PREFERRED EMBODIMENTS

Figure 1:
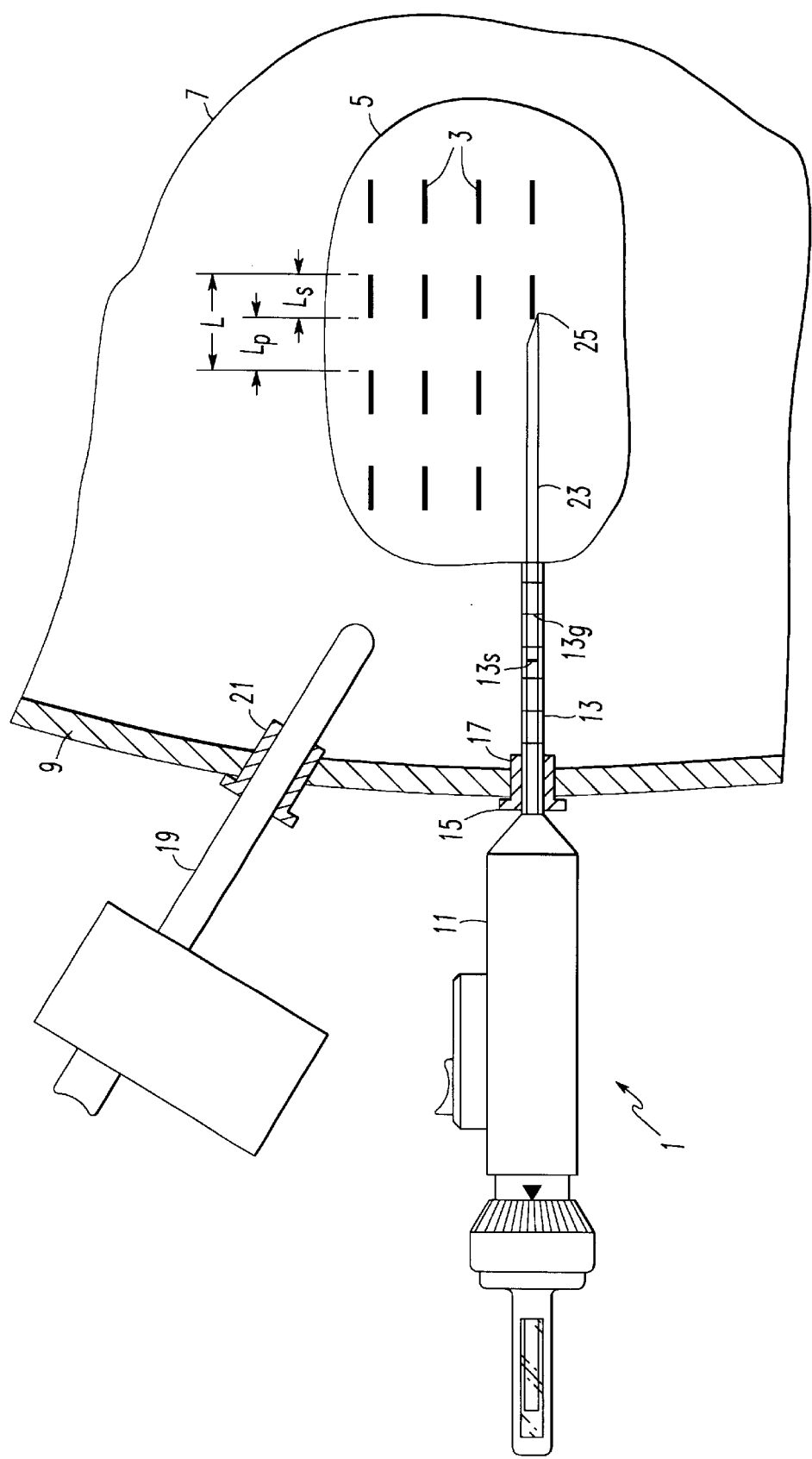
FIG. 1 is a schematic view illustrating use of the apparatus in accordance with the invention to deposit implants in a tumor such as an intrathoracic tumor with the aid of a thoracoscope to align the apparatus with the tumor.

The invention is directed to an apparatus and method for depositing implants in soft tissue and particularly, but not necessarily, tumors. The term implant as used throughout refers to non-resorbable, permanent metal, or equivalent material containing a radioisotope, commonly referred to as radioactive seeds. It also refers to such materials used for brachytherapy. The term implant further includes capsules containing, or discrete carriers such as pellets coated with, vectors containing nucleic acid sequences encoding a gene of interest. The vectors can include viral and non-viral vectors. Appropriate vectors include but are not limited to adeno-associated virus vectors, adenovirus vectors, retroviral vectors, plasmids, lenti virus vectors, herpes virus vectors and any other form of viral or sub-cellular organism used as a vector for inserting transgenes. Such vectors could also include, for example, yeast artificial chromosome, human chromosome fragments, or sub-cellular components which can be used to introduce a gene of interest to soft tissue cells. Non-viral means for introducing nucleic acid sequences include but are not limited to liposomes, calcium phosphate, electroporation, and DEAE-dextran. Naked nucleic acid can also be introduced into the soft tissue including, for example, RNA, DNA, cDNA, oligonucleotides and anti-sense RNA. The implants can also contain or be coated with other therapeutic or prophylactic agents, such as a pharmaceutical or pharmacological material, a chemical or other molecular material which can be used to elicit a biological or physiological response.

The "gene of interest", as that term is used herein, refers to any gene encoding a protein, peptide, or fragment thereof that the user desires to introduce to the soft tissue cells. Accordingly, the gene of interest will vary depending on the needs of the user, based upon such things as the illness or condition for which the gene is being introduced and the soft tissue being targeted. For example, the gene can encode a protein, peptide or fragment thereof that functions in a therapeutic or prophylactic manner in the soft tissue transduced by the gene. Examples include, but are not limited to, genes encoding for: an antisense molecule for any of the growth factors, such as any form of the transforming growth factors, fibroblast growth factors, or insulin-like growth factors; an antisense molecule for any growth factor receptor; an antisense molecule for any signal transduction molecule, such as a janus associate kinase (JAK) or STAT kinase; a growth inhibiting or apoptosis-inducing gene that would either limit cell growth or induce cell death; an apoptosis-inducing protein such as BAX (a non-dephosphorelatable form of BAD); a protein that inhibits a cell's antioxidant defenses, such as antisense for manganese superoxide dismutase, glutathione peroxidase, or any other naturally occurring anti-apoptotic protein or peptide; a protein, peptide or fragment thereof that limits vascularization; a protein, peptide or fragment thereof that prevents an angiogenic response, such as basic fibroblast growth factor (bFGF), human growth factor (HGF), or vascular endothelial growth factor (VEGF), by effecting endothelial cells within a tumor or inhibiting an angiogenic product; a cytokine, such as granulocyte macrophage colony stimulating factor (GM-CSF), any of the interleukins (IL), especially IL-11, IL-7 and IL-12, the growth factors listed above, growth hormone, bone morphogenetic proteins, and any other cytokine or chemokine that elicits a response in cytotoxic T cells, NK cells, dendritic cells, macrophages, polymorphonucleoleukocytes, or other immune effector cells that lyse tumors; and toxins that kill tumor cells.

The implants can also contain or have coated thereon other materials or chemicals which would have a biological effect on the soft tissue. For example, the implants can comprise: cellular material; tissue culture medium and NK cells sensitized ex vivo to kill a tumor; other sensitized immune effector cells such as dendritic cells or cytotoxic T cells; chemotherapeutic drugs such as anthracycline antibiotics, antifolate, toxol or other agents or derivatives; and protective agents, such as superoxide dismutase, glutathione peroxidase, or cytokines known to induce protective effects within normal tissue, such as HGF, IL-1 or GM-CSF, insertable into certain soft tissue, such as the liver or pancreas, to protect this tissue from the cytotoxic damage during radiotherapy to adjacent or associated organs.

It is also a feature of the present invention that the capsules be formulated with the appropriate resorbable material so as to effect a timed-release of the therapeutic or prophylactic agent in the soft tissue. In this manner, for example, drugs could be released slowly over time, providing a continuous exposure of these drugs to the effected soft tissue. The preparation of such capsules is within the skill of one practicing in the pharmaceutical arts.

The apparatus is particularly suitable for inserting an implant into specific sites in the abdomen or thorax where the introduction is carried out through a puncture wound and monitored by laparoscopic or thoracoscopic visualization of alignment of the device. It is also suitable for implanting radioiodine or radioactive palladium seeds in the prostate for prostate brachytherapy. In addition, it is suitable for use of female patients with carcinoma of the vulva, uteri, cervix, endometrium, or ovary with intravaginal introduction of radioisotope-containing implants or seeds. The apparatus is further suitable for treating tumor volumes reached by intrarectal, intraoral or intra-esophageal administration of the implants. It could be further used where the patient is a fetus within the uterine cavity and the implants are a resorbable material designed to implant transgenes for in utero gene therapy for the treatment or modification of inheritable diseases.

FIG. 1 illustrates application of the implanter apparatus 1 to depositing implants 3 in soft tissue located in a cavity defined by an external wall. In this case, the soft tissue 5 is a tumor located in the thorax 7 defined by the chest wall 9. The apparatus 1 includes a sleeve 11 with a tubular extension 13 which is inserted through a trochar 15 inserted through a small incision 17 in the chest wall. A thoracoscope 19 is inserted through an adjacent small incision 21 so that the physician can align the implanter apparatus 1 with the tumor 5. As will be described, the implanter apparatus includes an introducer 23 having a sharpened distal end 25 which penetrates the tumor. The introducer is inserted into the tumor to the depth at which the most distant implant is to be deposited. The introducer is then incrementally withdrawn to deposit a plurality of implants in a row. The length of the implants is $L_s$ and the spacing between implants is $L_p$. As will be described, the spacing $L_p$ is easily adjustable. By repositioning the implant apparatus 1 using the thoracoscope 19, additional rows of implants 3 can be deposited within the tumor 5. It will be clear to those skilled in the art that laparoscopic techniques can similarly be used to deposit implants in intraabdominal soft tissue. Preferably, the tubular extension 13 is transparent and is provided with a depth graticule 13g which cooperates with a scribe lines 1 on the introducer to allow the surgeon to monitor the depth of penetration of the introducer 23, and therefore the successive points of deposit of the implants 3, in the tumor 5.

The preferred embodiment of the implant apparatus 1 is illustrated in FIGS. 2, 3A–3C, 4–6. The apparatus 1 includes the sleeve 11 with its tubular extension 13 and a cartridge unit 27 which incorporates the introducer 23. The cartridge unit 27 can be used by itself as will be described; however, preferably it is inserted into the sleeve 11 with the introducer 23 extending through the tubular extension 13 as indicated in the partially assembled view of FIG. 2.

Figure 3A:
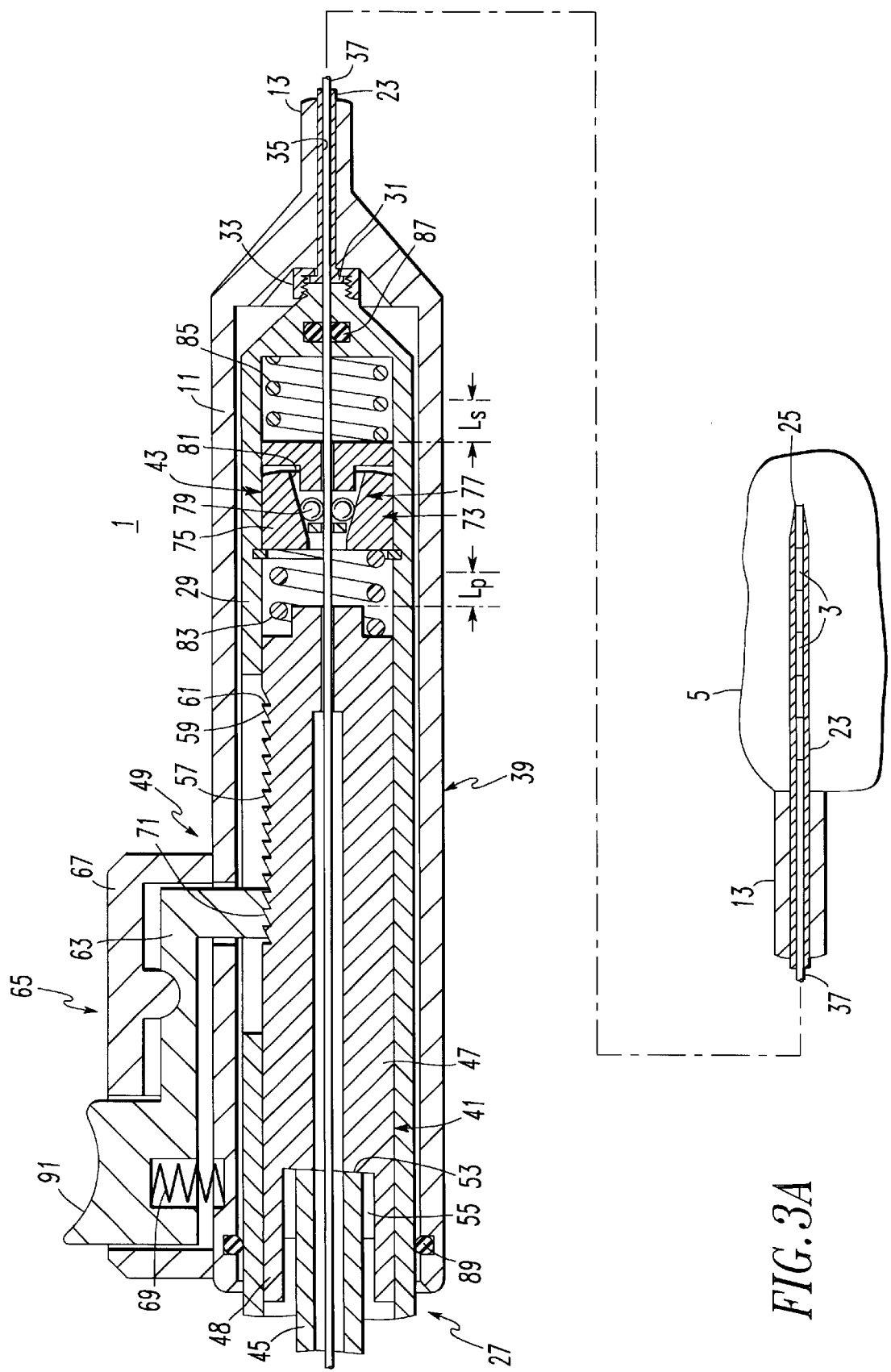
FIGS. 3A and 3B together illustrate a longitudinal section through the apparatus of FIG. 2 shown assembled but in the unactuated initial state taken along the respective planes shown in FIG. 3C.
Figure 3B:
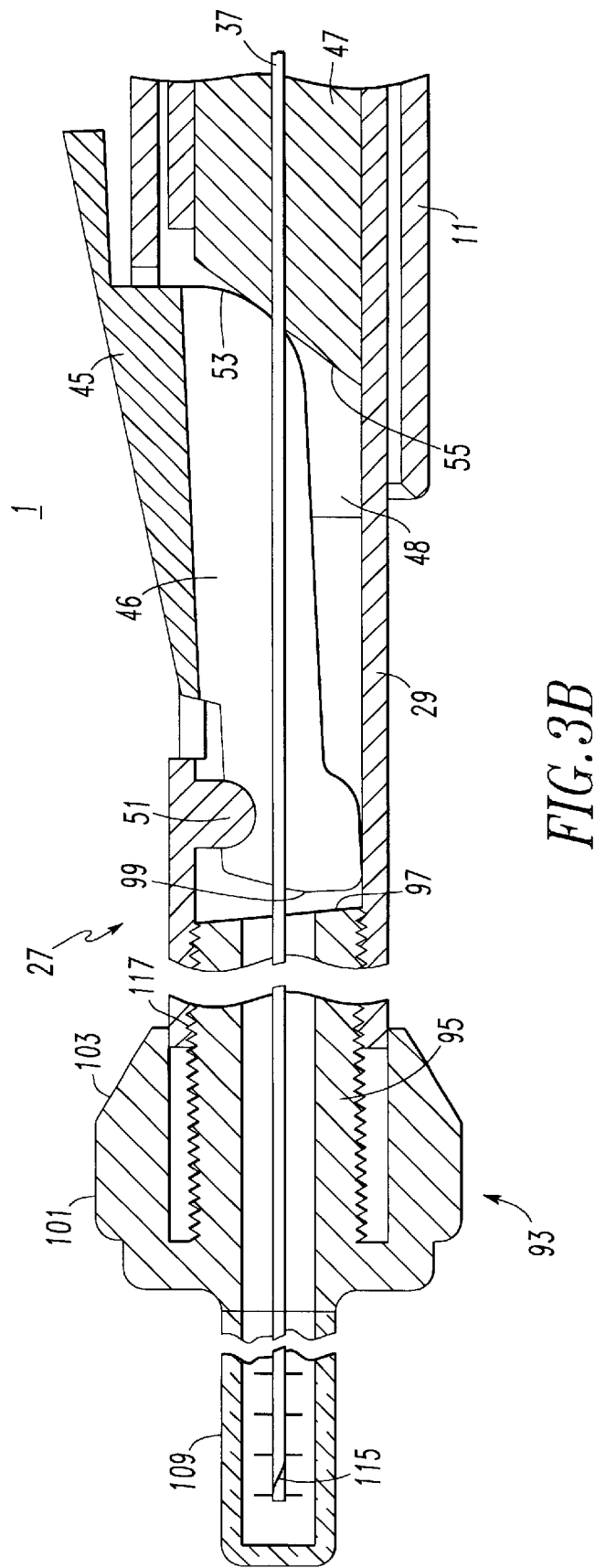

Referring particularly to FIGS. 3A and 3B, the cartridge unit 27 includes a tubular member 29 which forms an enlarged proximal end of the introducer 23. For manufacturing purposes the tubular member is a separate part to which the introducer is attached by a hickey nut 33 which clamps a flange 31 on the introducer 23 against the tubular member 29. This also allows the introducer to be a single-use item which may be provided already loaded with a supply of implants. The introducer 23 has a longitudinal passage 35 in which the implants 3 are retained. An obturator 37 is inserted into the passage 35 from the proximal end and bears against the implants 3. The distal end 25 of the introducer 23 is configured in a manner to be described to retain the implants 3 in the passage 35.

The apparatus 1 deposits the implants 3 by repetitively, incrementally withdrawing the introducer 23. During the first part of this incremental withdrawing motion, the obturator is held stationary relative to the introducer. This results in the dropping off of an implant as illustrated in the lower part of FIG. 4. During a second portion of the incremental withdrawal of the introducer 23, the obturator 37 is coupled to and moves with the introducer over the distance $L_p$. This distance $L_p$ provides the spacing between implants. It can be appreciated that with successive incremental withdrawals of the introducer inward with the sleeve 11 over the distance L, a plurality of the implants 3 are deposited with a spacing $L_p$ between implants.

This incremental withdrawal of the introducer and coupling and decoupling of the obturator to the introducer is effected by an operating mechanism 39. This operating mechanism 39 includes an actuator 41 for incrementally withdrawing the introducer over the distance L and a coupler 43 for automatically coupling the obturator 37 to the introducer after the introducer has moved the length of a seed $L_s$ and over the spacing distance $L_p$. The actuator 41 includes a trigger 45, a slide 47 slidable in the tubular member 29 and a one-way clutch 49 for selectively locking the slide 47 to the sleeve 11. The trigger 45 is pivotally mounted by a pivot mount 51 inside the tubular member 29 and has a longitudinal groove 46 through which the obturator 37 extends. The trigger has a trigger cam surface 53 which engages an inclined slide cam surface 55. As can be appreciated from FIGS. 3 and 4, actuation of the trigger results in movement of the slide 47 forward or to the right in FIG. 3 relative to the tubular member 29. A pair of rearwardly extending wings 48 on the slide 47 straddle the trigger 45 to prevent the slide from rotating within the tubular member.

The one-way clutch 49 includes a rack 57 having a number of ratchet teeth 59 extending along the slide 47. These ratchet teeth 59 have an engagement surface 61 facing forward. The one-way clutch 49 further includes a pawl member 63 pivotally mounted for rotation about a pivot 65 in a housing 67 on the sleeve 11. A helical compression spring 69 biases teeth 71 on the pawl member 63 into engagement with the ratchet teeth 59 on the slide. Thus, it can be appreciated that when the trigger is actuated, with the slide held stationary relative to the sleeve 11 by the one-way clutch 49, the tubular member 29 on which the trigger is mounted is withdrawn rearward relative to the sleeve 11. As the introducer 23 is fixed to the tubular member 29, it is also withdrawn rearward relative to the sleeve 11.

The coupler 43 which automatically couples the obturator 37 to the introducer after the seed has been deposited, includes a holding device 73 formed by a shuttle 75 slidable within the tubular member 29 and a directional clutch 77 which allows the obturator to move forward relative to the shuttle but not rearward. A suitable directional clutch is a ball clutch which includes a number of ball bearings 79 which are jammed against the obturator 37 by a tubular ball race 81 by relative forward movement of the shuttle 75.

The holding device 73 for the obturator 37 further includes a decoupling spring 83 between the slide 47 and the shuttle 75 and a shuttle return spring 85 between the shuttle and the forward end of the tubular member. The decoupling spring 83 and shuttle return spring 85 are helical compression springs with the decoupling spring being stronger than the shuttle return spring. The holding device 73 for the obturator also includes a slip clutch 87 which may take the form of an O-ring seated in the tubular member 29 and which bears against the obturator 37.

Figure 4:
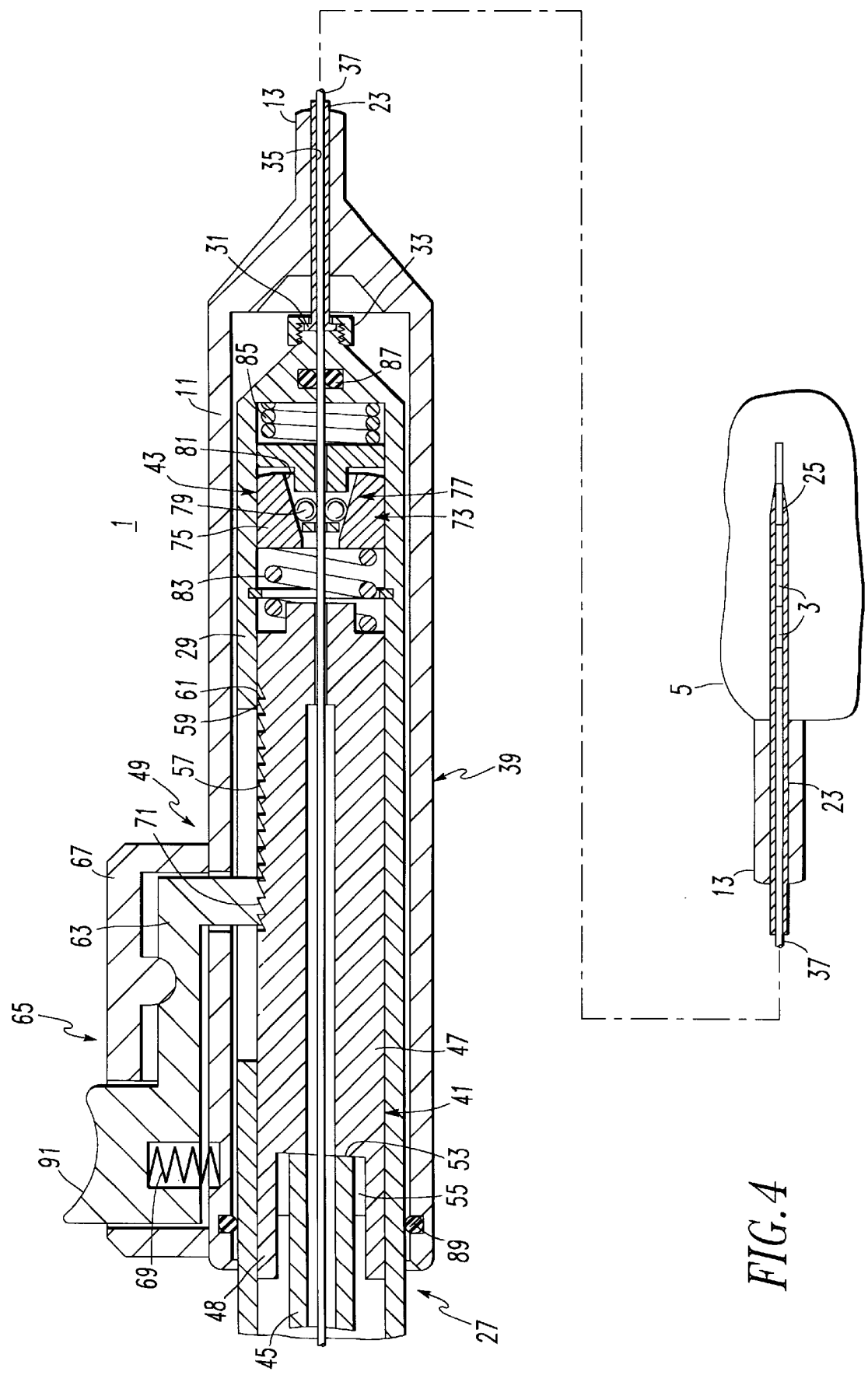
FIG. 4 is a partial view similar to FIG. 3A but showing the parts in the partially actuated condition where an implant has just been deposited.
Figure 5:
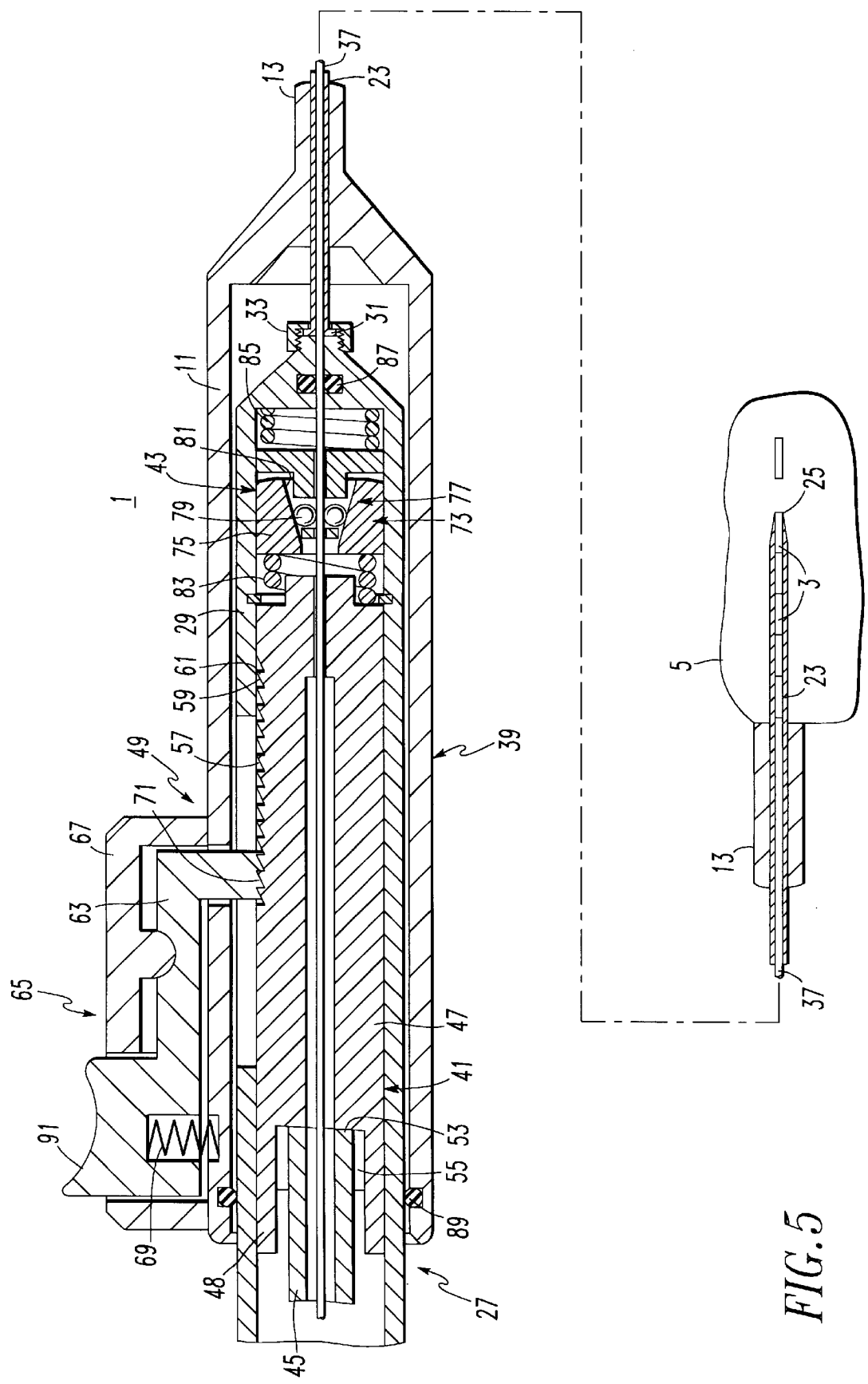
FIG. 5 is a partial sectional view similar to FIG. 4 with the parts shown in the position in which the trigger has been fully depressed to provide the spacing between implants.

The operation of the holding device 73 is as follows. When the trigger is actuated and the tubular member 29 moves rearward, the decoupling spring 83 holds the shuttle 75 stationary relative to the slide 47 and therefore also to the sleeve 11. This results in compression of the shuttle return spring 85. Thus, the introducer 23 is withdrawn while the obturator 37 is held stationary relative to the tumor by the directional clutch 77. The resultant relative movement between the introducer and obturator deposits an implant 3 in the tumor. After the tubular member, and therefore the introducer, have been withdrawn the distance $L_s$, the shuttle return spring 85 becomes fully compressed as shown in FIG. 4 and the shuttle 75 seats against and is carried with the tubular member/introducer 23 for the remainder of the distance L, or $L_p$. As the shuttle 75 is withdrawn with the introducer 23, the ball clutch 77 relaxes its hold on the obturator 37 but the slip clutch 87 pulls the obturator rearward with the tubular member, and therefore, the introducer the distance $L_p$ as shown in FIG. 5 to set the spacing between implants.

Figure 6:
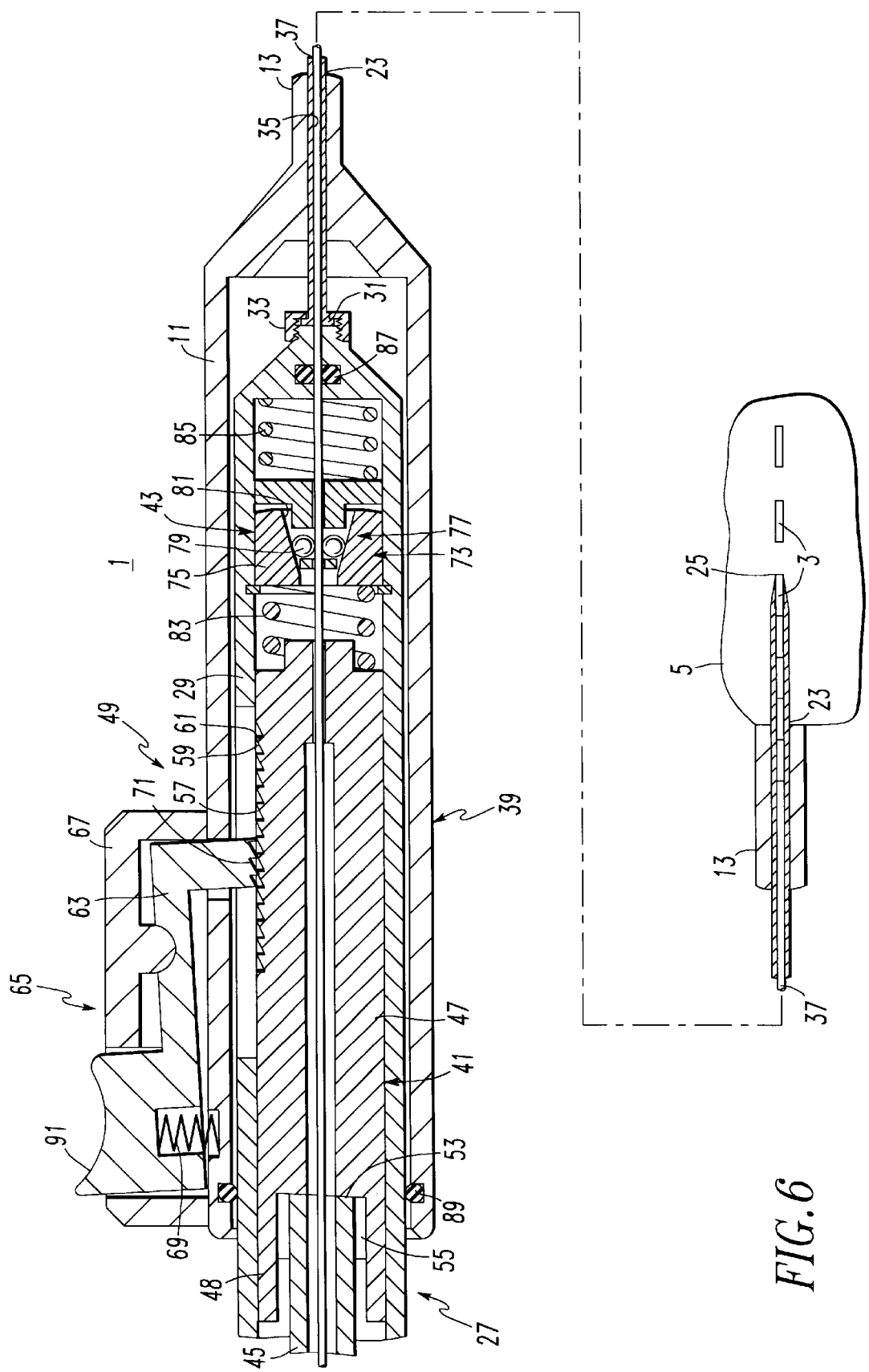
FIG. 6 is a partial sectional view similar to FIGS. 4 and 5 showing the position of the parts after the trigger has been released.

Release of the trigger 45 allows the decoupling spring 83 and the shuttle return spring 85 to expand thereby applying a rearward force on the slide 47 and a forward reaction force on the tubular member 29. This reaction force is resisted by an O-ring 89 in the sleeve 11 engaging the tubular member 29. Therefore, the tubular member 29 remains stationary relative to the sleeve 11 and the slide 47 moves rearward with the pawl member 63 sliding over the rearward moving ratchet teeth 59 as shown in FIG. 6.

In summary, each time the trigger 45 is actuated, the tubular member 29 and introducer 23 are withdrawn the distance $L_s$ to deposit an implant 3. The obturator 37 remains stationary until the implant is dropped and then moves with the introducer to provide the spacing $L_p$ between implants. Upon release of the trigger 45, the slide 47 moves rearward to position the parts for the next actuation. By repetitively actuating the trigger 45, a row of implants 3 are deposited in the soft tissue 5 as described in connection with FIG. 1. At the end of a row, a reset button 91 is depressed to disengage the pawl member 63 from the rack 57 so that the cartridge unit 27 can be reinserted fully within the sleeve 11 in preparation for depositing another row of seeds as shown in FIG. 3A.

As pointed out, a feature of the apparatus in accordance with the invention is that the spacing $L_p$ between the deposited implants 3 is readily adjustable. In the preferred embodiment of the invention, this adjustability is provided by an arrangement which limits the total distance L that the slide 47 can move within the tubular member 29. With the distance $L_s$ equal to the length of the implant remaining constant, this necessarily adjusts the spacing $L_p$ between the implants. Preferably, the adjustment mechanism 93 is provided in the form of a tubular adjustment member 95 threaded onto the free end of the tubular member 29 as shown in FIG. 3B. The forward end of the tubular adjustment member 95 has surface 97 which engages an adjustment cam surface 99 on the rear of the trigger 45. Thus, the axial position of the tubular adjusting member 95 sets a limit on the stroke of the trigger which, in turn, through engagement of the trigger camming surface 53 with the slide cam surface 55, limits the rearward movement of the slide and therefore the spacing $L_p$. The tubular adjusting member 95 has a cylindrical cap 101 with a tapered skirt 103 which extends forward over the free end of the tubular member 29. Indicia 105 on the skirt cooperate with a scribe line 107 on the tubular member to provide a quantitative measure of the spacing $L_p$ as can be seen in FIG. 2. Hence, the user can easily adjust the spacing $L_p$ between implants by rotating the tubular adjusting member 95 to the desired setting.

The apparatus 1 also includes a housing 109 for protecting the obturator 37 which extends rearward out of the end of the tubular member 29, and especially when the introducer 23 is fully loaded with implants. In the embodiment shown in FIGS. 2 and 3B, this housing 109 is formed integrally with the tubular adjustment member 95. In order to provide an indication of the number of implants which have been deposited, the housing 109 can be made transparent (FIG. 3B) or be provided with a longitudinally extending window 110 (FIG. 2), which allows observation of the proximal end of the obturator 37. A graticule 113 on the housing can then provide a numerical indication of the number of implants implanted by observing the position of the obturator 37 relative to the scale. Because the housing 109 is integral with the tubular adjustment member 29, a helical scribe line 115 is provided adjacent the proximal end of the obturator to maintain the accuracy of the count of implants regardless of the spacing between implants selected. This helical scribe line 115 has the same pitch as the thread 117 on the tubular adjustment member 95, but the pitch of the scribe line 115 has been exaggerated in FIG. 3B for clarity.

Figure 7:
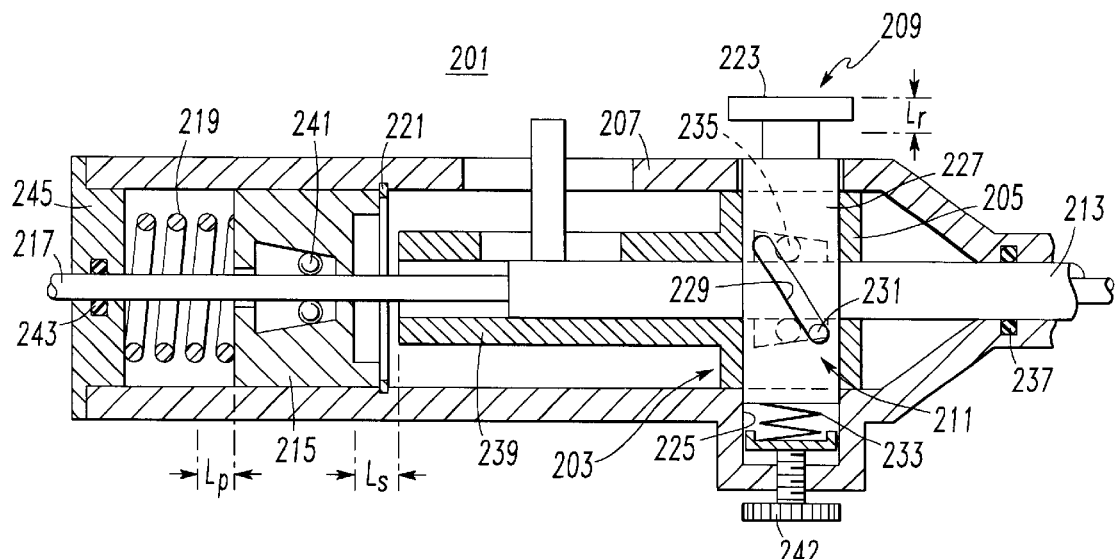
FIG. 7 is a longitudinal sectional view through apparatus in accordance with a second embodiment of the invention.

A second embodiment of the apparatus 201 is illustrated in FIG. 7. In this embodiment, the operating mechanism 203 includes a carriage 205 slidable within the sleeve 207 and a trigger assembly 209 for reciprocating the carriage 205 forward and rearward within the sleeve 207. The operating mechanism 203 further includes a trigger coupling 211 coupling the introducer 213 to the carriage 205 only as the carriage moves rearward.

The operating mechanism 203 of the implanter apparatus 201 also includes an aft shuttle 215 which is slidable within the sleeve 207 rearward of the carriage 205. The aft shuttle 215 couples the obturator 217 to the introducer 213 after the introducer has moved the length of an implant $L_s$. The aft shuttle 215 is positioned for engagement by rearward movement of the carriage 205 by a helical compression spring 219 which biases the aft shuttle forward against a stop formed by a snap ring 221.

The trigger assembly 209 includes a trigger member 223. The trigger member 223 is mounted in a slot 225 formed in the sleeve 207 for rectilinear movement generally transverse to the introducer 213. The trigger member 223 includes a bifurcated center portion 227 which straddles the carriage 205. The trigger coupling 211 includes a diagonal groove 229 in the body 227 of the trigger member, and a coupling pin 231 projecting laterally from the carriage 205 and engaging the diagonal groove 229. A helical compression spring 233 biases the trigger member 223 upward as viewed in FIG. 7. The trigger assembly 209 is actuated by pressing downward on the trigger member 223. As the groove 229 is diagonal to both the rectilinear motion of the trigger member 225 and movement of the carriage 205, the downward movement of the trigger member 223 results in rearward movement of the carriage 205. Upon release of the trigger member 223, the spring 233 biases the trigger member 223 upward and the carriage 205 forward. A one-way clutch in the form of the ball clutch 235 couples the introducer 213 to the carriage 205 only as the carriage moves rearward. As the carriage 205 moves forward, a slip clutch in the form of an O-ring 237 seated in the sleeve 207 overcomes the friction force tending to pull the introducer 213 forward along with the carriage 205.

The carriage 205 has a collar 239 which engages the aft shuttle 215 after the carriage has moved rearward by the distance $L_s$. When the collar 239 engages the aft shuttle 215, the aft shuttle begins to move rearward and through the one-way ball clutch 241 pulls the obturator 217 rearward with it. Thus, the obturator 217 and introducer 213 move rearward together to provide the spacing $L_p$ between implants. When the trigger member 223 is released, the carriage 205 is moved forward by the spring 233 which raises the trigger body 227 causing the coupling pin 231 on the carriage to be moved forward by translation of the diagonal coupling slot 229. The spring 219 also moves the aft shuttle 215 forward against the stop 221 in preparation for the next actuation of the trigger member. As shown in FIG. 7, the spacing $L_p$ between implants is made adjustable by adjusting the stroke $L_r$ of the trigger member which determines the length of the overall withdrawal L of the introducer 213 with each trigger actuation. The stroke of the trigger $L_r$ is made adjustable by a thumb screw 242 which limits downward travel of the trigger member. It will be appreciated, that alternatively the spacing $L_p$ could be made adjustable by a tubular adjustment member on the end of the sleeve 207 similar to that described in connection with the embodiment shown in FIG. 2. A slip clutch formed by the O-ring 243 seated in an end cover 245 on the sleeve 207 prevents forward movement of the obturator 217 as the aft shuttle 215 is repositioned forward upon release of the trigger mechanism. It will be further appreciated that the apparatus 201 of FIG. 7 can also have an indicator of the number of implants deposited similar to that shown in the embodiment of FIG. 2. Because the adjustment of the spacing $L_p$ is provided by the thumb screw 242, the housing for the obturator does not move with the adjustment, and therefore an annular rather than a helical scribe line is all that is needed on the obturator. In fact, the end of the obturator can be read against the graticule to determine the number of implants deposited.

Figure 8:
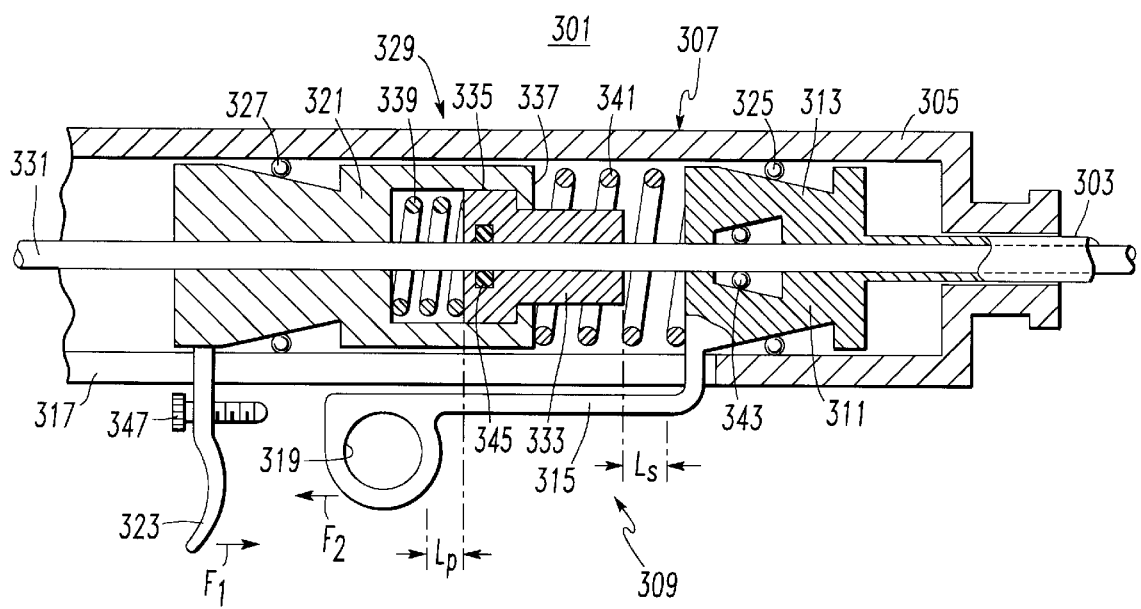
FIG. 8 is a longitudinal section through apparatus in accordance with a third embodiment of the invention.

A third embodiment of an implanter apparatus 301 in accordance with the invention is illustrated in FIG. 8. In this embodiment, the introducer 303 is incrementally withdrawn rearward within the sleeve 305 by an operating mechanism 307 in the form of a walking mechanism 309 which walks the introducer 303 rearward in repetitive, small steps equal to the distance L. The walking mechanism 309 includes a first actuating member 311 having a body section 313 secured to the proximal end of the introducer 303 and slidable within the sleeve 305. The first actuating member 311 also has an elongated grip 315 which extends outward through a longitudinal slot 317 in the sleeve 305 and then rearward where it terminates in a finger hole 319.

The walking mechanism 309 of the implanter 301 also includes a glide 321 slidable within the sleeve 305 rearward of the first actuator body 313. A second actuating member 323 connected to the glide 321 projects outward through the slot 317 and is aligned with the finger hole 319 of the first actuating member 311. A first one-way clutch in the form of ball clutch 325 blocks forward movement of the first actuating member 311, and therefore the introducer 303, which is fixed to it. A second one-way clutch in the form of ball clutch 327 prevents forward movement of the glide 321, and therefore the second actuating member 323.

The operating mechanism 307 also includes a coupling device 329 for automatically coupling the obturator 331 to the introducer 303 after the distance $L_s$. This coupling device 329 includes a shuttle 333 which is captured by, but slidable relative to, the glide 321. As shown in FIG. 8, the shuttle 333 has a flange 335 on the rearward end which is engaged by a radial inward lip 337 on the glide which forms a forward stop for the shuttle relative to the glide. A helical compression spring 339 biases the shuttle 333 forward against the stop formed by the radial lip 337. A second, stronger helical compression spring 341 biases the first actuator body 313 and the glide 321 apart. A third clutch, preferably in the form of the ball clutch 343 provided on the body 311 of the first actuating member, restricts inward movement of the obturator 321 relative to the introducer 303. A fourth clutch 345 mounted in the shuttle 333 couples the obturator 321 to the shuttle 333.

The operation of the implanter apparatus 301 is as follows. With the parts in the unactuated position as shown in FIG. 8, the user squeezes the finger hold 319 of the first actuating member and the second actuating member 323. This produces equal and opposite forces $F_1$ in the forward direction on the second actuating member 323 and $F_2$ in the rearward direction on the first actuating member 311 through the finger hold 319. As the ball clutch 327 prevents forward movement of the glide 321 and therefore the second actuating member 323 in response to the force $F_1$, the first actuating member 311 and therefore the introducer 303 are drawn rearward. The obturator 321 is held stationary by the clutch 345 and the spring 339. When the introducer 303 has been withdrawn the length of an implant $L_s$ the aft shuttle 333 is contacted and begins to move rearward compressing the spring 339. The clutch 345 couples the obturator 321 to the shuttle 333 so that the introducer 303 and obturator 321 move rearward together through the distance $L_p$.

When the user relaxes the forces applied to the actuating members, the spring 341 applies a force tending to push the first actuating member 311 forward and the glide 321 and second actuating member 323 rearward. As the clutch 325 prevents forward movement of the first actuating member 311 and therefore the introducer 303, the glide 321 is moved rearward. The shuttle 333 is held against the first actuating member body 313 by the spring 339 until the flange 335 on the shuttle is engaged by the radial lip 337 on the glide, and the shuttle is pulled rearward with the glide. The obturator is not dragged rearward with the glide 321 because the clutch 343 overpowers the clutch 345 and holds the obturator 321 stationary relative to the introducer 303.

Adjustment of the spacing $L_p$ between implants is provided by an adjustment screw 347 which limits movement of the first actuating member 311 and the second actuating member 323 toward each other.

Figure 9E:
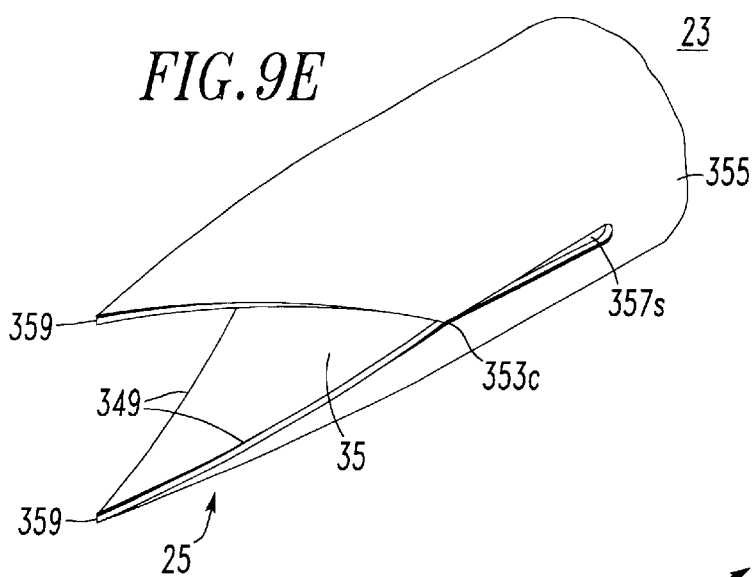

Another aspect of the invention is the configuration of the distal end 25 of the introducer 23. Examples of various configurations of the distal end 25 of the introducer 23 possible in accordance with the invention are shown in FIGS. 9A–9G. The distal end 25 performs two functions: 1) penetration of the soft tissue, and 2) containment of the implants for controlled discharge. The first function is accomplished by sharpening the distal end 25 such as by a single 347 or double 349 chamfer. Containment of the implants is implemented by an integral restraining mechanism 351 incorporated into the distal end 25 which reduces the passage 35 to an inscribed circular opening which is smaller in lateral dimension than the implants 3, yet is resiliently expandable for ejection of implants by the obturator 37. The restraining mechanism 351 includes radially inwardly directed deformations 353 in the wall 355 of the tube forming the introducer 23 and strain relief cuts 357 in the introducer tube. The deformations 353 may be a crimp 353c in the tube or dimples 353d. The cuts are either slits 357s extending through the introducer wall 355 or kerfs 357k extending only partially through the wall. Preferably, these slits 357s or kerfs 357k are longitudinal, and they may be open ended, in that they extend to the distal end of the introducer, or they are closed, stopping short of the distal end. In the example shown in FIG. 9A, two diametrically opposite open slits 357s extend longitudinally through the tube wall 355. One half 25a of the split end is chamfered at 347 and the other 25b maintains a square end but is tapered downward to a thin edge. The two halves 25a and 25b are crimped at 353c. In the configuration of FIG. 9b, a single open longitudinal slit 357s extends from the innermost point of a single chamfer 347. A single open kerf 357k is located diametrically opposite the slit 357s and the distal end 25 is crimped at 353c.

A pair of diametrically opposite open longitudinal slits 357s are centered on a single chamfer 347 on the distal end 25 of the introducer 23 shown in FIG. 9C. FIG. 9D illustrates a preferred manner of forming the crimp as applied to the embodiment of FIG. 9C. The triangle crimp 353t produces an inscribed circle 363 having a diameter $d_1$ which is less than the diameter $d_2$ of the passage 35 in the tubular introducer. However, the strain relief slits 357s allow the sharpened distal end 25 to expand and eject an implant pushed forward by movement of the obturator relative to the introducer. In the embodiment of FIG. 9E, a double chamfer 349 produces a pair of pointed ends 359. A single open longitudinal slot 357 extends from a root between the two pointed ends 359 which are crimped at 353c.

Figure 9F:
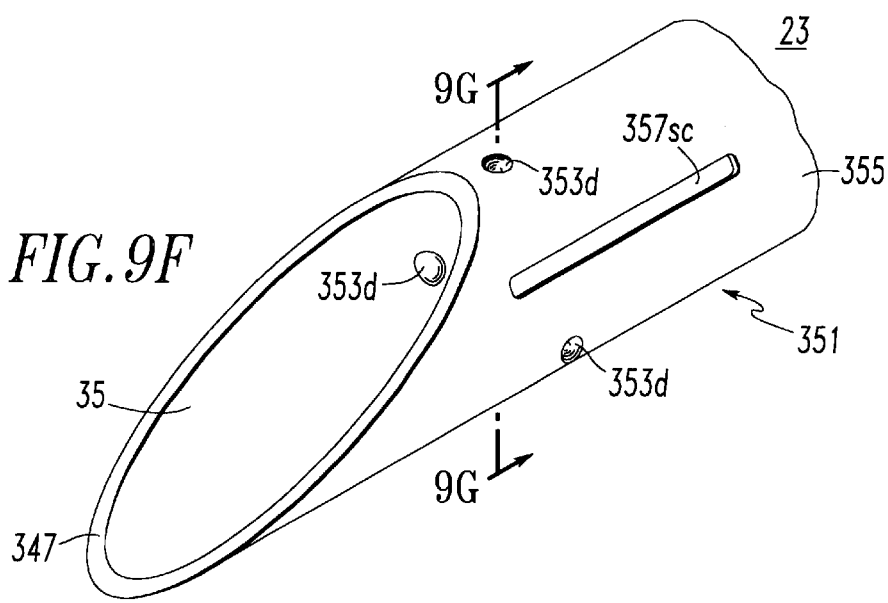
Figure 9G:
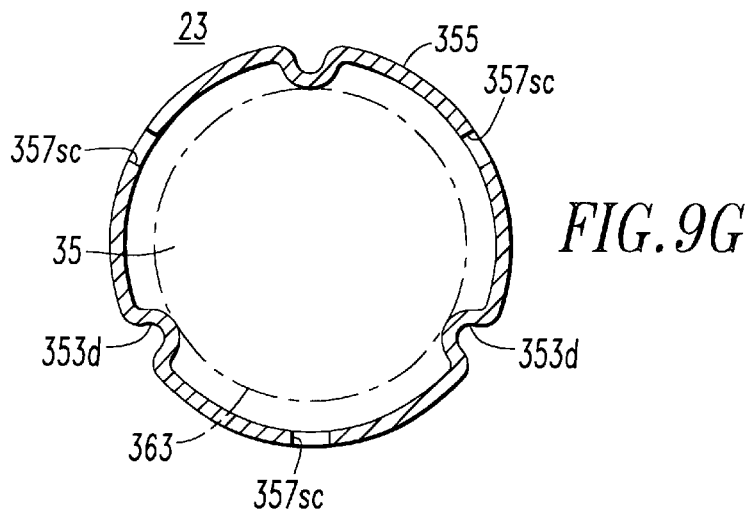
FIG. 9G is a cross-section through the introducer of FIG. 9F.

FIGS. 9F and 9G illustrate another embodiment of the restraining mechanism 351 incorporated into the sharpened distal end 25 of the introducer. Here, the deformations take the form of three circumferentially spaced dimples 353d, and the strain relief cuts are three equally spaced closed, longitudinal slits 357s. As shown in FIG. 9G, the dimples 353d reduce the passage 35 to an inscribed circle 363 having a diameter smaller than the diameter of an implant. Again, the slits 357sc allow the distal end 25 to resiliently expand for ejection of implants.

Preferably, as previously discussed, the introducer 23 is a disposable component which comes packaged with a supply of implants 3 contained in the passage 35. The replacement introducer is secured to the tubular member 29 by the hickey nut 33 in the embodiment of FIGS. 2–6.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

What is claimed is:

1. An apparatus for depositing implants having an implant length $L_s$ in soft tissue, said apparatus comprising:

an introducer comprising an elongated tube having a distal end insertable into the soft tissue and a passage extending from a proximal end to said distal end in which a plurality of implants are adapted to be retained;

an obturator slidable within said passage in said introducer from said proximal end and bearing against said implants;

a sleeve through which said introducer slidably extends; and an operating mechanism comprising means repetitively, incrementally withdrawing said introducer reward relative to said sleeve a distance L and means automatically coupling said obturator to said introducer after said introducer has been withdrawn a distance $L_s$ equal to the length of the implant to withdraw said obturator with said introducer for the remainder of said distance L equal to $L_p$, whereby implants are deposited in said soft tissue with a spacing equal to $L_p$.

2. The apparatus of claim 1 wherein said operating mechanism includes adjusting means for adjusting said distance $L_p$.

3. The apparatus of claim 1 adapted for depositing implants in soft tissue located in a cavity having an external wall, said sleeve having a tubular extension insertable through an incision in said external wall for aligning said introducer which extends through said tubular extension with said soft tissue.

4. The apparatus of claim 1 wherein said introducer has an enlarged proximal end forming a tubular member which is received in said sleeve, and wherein said means incrementally withdrawing said introducer rearward comprises an actuator including a trigger supported on said tubular member, a slide slidable forward relative to said tubular member upon actuation of said trigger, and a one-way clutch locking said slide to said sleeve as said trigger is actuated to incrementally withdraw said tubular member rearward said distance L with respect to said sleeve, and said means automatically coupling said obturator to said introducer comprises holding means engaged by said slide holding said obturator stationary relative to said sleeve until said introducer has been withdrawn said distance $L_s$ and a slip clutch through which said obturator slips as said introducer moves said distance $L_s$ and which couples said obturator to said introducer for movement with said introducer over said distance $L_p$.

5. The apparatus of claim 4 wherein said one-way clutch comprises a rack on one of said slide and said sleeve, and a pawl member on the other of said rack and said slide and said sleeve which engages said rack.

6. The apparatus of claim 5 wherein said means incrementally withdrawing said introducer further includes means biasing said slide rearward on release of said trigger, and means resisting rearward movement of said tubular member relative to said sleeve, said rack having teeth over which said pawl member slides as said slide moves rearward.

7. The apparatus of claim 6 wherein said one-way clutch further includes a pawl mount disengaging said pawl member from said rack for selectively repositioning said tubular member forward relative to said sleeve.

8. The apparatus of claim 7 wherein said rack is on said slide and said pawl mount mounts said pawl member on said sleeve.

9. The apparatus of claim 4 wherein said means holding said obturator stationary relative to said sleeve comprises a fore shuttle slidable in said tubular member, and a directional clutch blocking inward movement of said obturator relative to said fore shuttle.

10. The apparatus of claim 9 wherein said means holding said obturator further includes a decoupling spring between said slide and said fore shuttle holding said fore shuttle stationary relative to said sleeve while said introducer moves said distance $L_s$ relative to said sleeve and until said fore shuttle seats relative to said tubular member and moves with said tubular member, and therefore said introducer, over said distance $L_p$ against said decoupling spring.

11. The apparatus of claim 10 wherein said means holding said obturator further includes a return spring between said fore shuttle and said tubular member biasing said fore shuttle away from seating relative to said tubular member, said decoupling spring being stronger than said return spring.

12. The apparatus of claim 4 wherein said operating mechanism further includes adjusting means for adjusting said distance $L_p$.

13. The apparatus of claim 12 wherein said means for adjusting said distance $L_p$ comprises means limiting movement of said slide.

14. The apparatus of claim 13 wherein said means for limiting movement of said slide comprises a tubular adjusting member threaded onto an inner end of said tubular member with an eccentric cam surface forming an adjustable stop limiting travel of said slide.

15. The apparatus of claim 14 including a housing for said obturator extending rearward from said tubular adjusting member and through which said obturator is visible, said housing having a graticule thereon providing a scale for indicating a count of implants deposited, and a helical scribe line on said obturator which registers with said graticule to indicate said count.

16. The apparatus of claim 4 wherein said one-way clutch comprises a rack on said slide and a pawl member mounted on said sleeve and engaging said rack to resist rearward movement of said slide, said holding means holding said obturator stationary relative to said sleeve comprises a fore shuttle slidable in said sleeve forward of said slide, and a directional clutch blocking rearward movement of said obturator relative to said fore shuttle, said holding means further including a decoupling spring between said slide and said fore shuttle holding said fore shuttle stationary relative to said slide while said introducer moves said distance $L_s$ at which point said fore shuttle seats relative to said introducer and moves with said introducer, a slip clutch between said introducer and said obturator through which said obturator slides while being held stationary relative to said sleeve by said fore shuttle and which moves said obturator with said introducer with said fore shuttle moving with said introducer, and a return spring biasing said fore shuttle away from seating relative to said tubular member, said rack having teeth over which said pawl member slides as said slide is driven rearward by said decoupling spring and return spring upon release of said trigger.

17. The apparatus of claim 16 including means adjusting said distance $L_p$ and comprising a tubular adjusting member threaded onto an inner end of said tubular member with an eccentric cam surface forming an adjustable stop engaging said trigger.

18. The apparatus of claim 1 wherein said means incrementally withdrawing said introducer comprises a carriage slidable within said sleeve, means reciprocating said carriage forward and rearward within said sleeve, and means coupling said introducer to said carriage only as said carriage moves rearward.

19. The apparatus of claim 18 wherein said means coupling said obturator to said introducer comprises a shuttle slidable in said housing rearward and forward, and means positioning said shuttle for engagement by and movement rearward with said carriage after said introducer has been moved rearward by said carriage said distance $L_s$.

20. The apparatus of claim 19 wherein said means positioning said shuttle for engagement by said carriage comprises first bias means biasing said shuttle toward the carriage, and a first stop against which said shuttle is biased by said first bias means setting said distance $L_s$ at which said shuttle is engaged by said carriage.

21. The apparatus of claim 20 wherein said operating mechanism includes adjusting means for adjusting said distance $L_p$ between said implants.

22. The apparatus of claim 21 wherein said adjusting means comprises means adjusting relative to said sleeve the position of a second stop against which said shuttle is seated by rearward movement of said shuttle.

23. The apparatus of claim 22 wherein said second stop is carried on a threaded member threaded onto said sleeve for movement rearward and forward relative to said sleeve.

24. The apparatus of claim 23 including indicator means associated with said threaded member providing an indication of said distance $L_p$.

25. The apparatus of claim 18 wherein said means reciprocating said carriage within said sleeve comprises a trigger assembly and a trigger coupling coupling said trigger assembly to said carriage.

26. The apparatus of claim 25 wherein said trigger assembly comprises a trigger member, means mounting said trigger member for rectilinear movement generally transverse to said introducer, and said trigger coupling means comprises a coupling pin on one of said trigger member and said carriage, and a coupling slot on the other of said trigger member and said carriage oriented at an angle to both said rectilinear movement of said trigger member and rearward and forward movement of said carriage and engaged by said coupling pin, and second bias means biasing said carriage forward.

27. The apparatus of claim 26 wherein said operating mechanism includes adjusting means for adjusting said distance $L_p$ between said implants.

28. The apparatus of claim 27 wherein said adjusting means comprises means adjustably setting a length $L_r$ of said rectilinear movement of said trigger member.

29. The apparatus of claim 27 wherein said means adjusting the length of $L_r$ of rectilinear movement of said trigger member comprises an adjustment screw against which said trigger member seats in driving said carriage rearward.

30. The apparatus of claim 1 wherein said means repetitively, incrementally withdrawing said introducer rearward relative to said sleeve comprises a walking mechanism incrementally walking rearward in said sleeve said distance L.

31. The apparatus of claim 30 wherein said walling mechanism comprises a first actuating member secured to said introducer adjacent said proximal end, a glide slidable in said sleeve rearward of said introducer, a second actuating member secured to said glide, first clutch means restraining forward movement of said introducer, second clutch means restraining forward movement of said glide, a spring biasing said introducer and glide apart, said first and second actuator members being positioned for movement toward each other in response to an external actuating force to draw said introducer rearward said distance L with said second clutch means holding said glide against forward movement, and said actuating members being separated by said spring with release of said external force to push said glide rearward with said first clutch means holding said introducer against forward movement.

32. The apparatus of claim 31 wherein said means automatically coupling said obturator to said introducer comprises a shuttle slidable relative to said glide between said introducer and said glide and engaged by and moved rearward with said introducer after said introducer has moved rearward said distance $L_s$, and means on said shuttle gripping said obturator for rearward movement with said shuttle.

33. The apparatus of claim 32 wherein said glide has a shuttle stop limiting forward movement of said shuttle relative to said glide and a second spring biasing said shuttle against said shuttle stop.

34. The apparatus of claim 33 wherein said walfing mechanism further includes third clutch means restraining rearward movement of said obturator relative to said introducer.

35. The apparatus of claim 34 wherein said walking mechanism further includes fourth clutch means restraining rearward movement of said obturator with said introducer until said shuttle is engaged by said introducer.

36. The apparatus of claim 31 wherein said walking mechanism further comprises adjusting means limiting movement of said first actuating member and second actuating member toward each other to adjust the distance $L_p$ between implants.

37. The apparatus of claim 1 wherein said operating mechanism further comprises implant indicator means indicating the number of implants implanted.

38. The apparatus of claim 37 wherein said operating mechanism includes a tubular adjusting member threaded onto a proximal end of said sleeve with threads of a selected pitch for adjusting said spacing $L_p$, and wherein said implant indicator means comprises a tubular obturator housing extending rearward from said tubular adjusting member into which said obturator extends and through which said obturator is visible, said obturator housing having a graticule thereon providing a scale for indicating a count of implants deposited, and a helical scribe line on said obturator having said selected pitch and which registers with said graticule to indicate said count.

39. The apparatus of claim 1 wherein said introducer has restraining means at said distal end for retaining said implants in said passage until pushed out of said distal end by inward movement of said introducer while said obturator remains stationary.

40. The apparatus of claim 39 wherein said restraining means comprises at least one radially inwardly directed deformation in said introducer, and at least one strain relief cut in said introducer adjacent said at least one radially inwardly directed deformation.

41. The apparatus of claim 3 wherein said tubular member has at least a section which is transparent and is provided with an introducer gauge, and said introducer has a depth indicator thereon which registers with said introducer gauge to provide an indication of the depth of penetration of said introducer into said soft tissue.

42. The apparatus of claim 1 wherein said introducer is sharpened at said distal end of said elongated tube, and has implant restraining means incorporated into said sharpened distal end for reducing said passage at said sharpened distal end to an inscribed opening smaller in lateral dimension than a lateral dimension of said at least one implant yet resiliently expanding said passage at said sharpened distal end for ejection of said at least one implant.

43. The apparatus of claim 42 wherein said implant restraining means comprises at least one radially inwardly directed deformation in said elongated tube, and at least one strain relief cut in said elongated tube adjacent said at least one radially inwardly directed deformation.

44. The apparatus of claim 43 wherein said at least one radially inwardly directed deformation in said elongated tube comprises a crimp.

45. The apparatus of claim 44 wherein said at least one radially inwardly directed deformation comprises a dimple.

46. The apparatus of claim 43 wherein said at least one strain relief cut comprises at least one longitudinal slit extending through said elongated tube.

47. The apparatus of claim 46 wherein said at least one elongated slit is open at said distal end of said introducer.

48. The apparatus of claim 46 wherein said at least one elongated slit is closed.

49. The apparatus of claim 43 wherein said at least one strain relief cut comprises a kerf partially extending through said elongated tube.

50. The apparatus of claim 42 wherein said sharpened distal end is formed by a single chamfer.

51. The apparatus of claim 42 wherein said sharpened distal end of said introducer is formed by a double chamfer.

52. The apparatus of claim 42 including a plurality of implants contained in said longitudinal passage.

53. Apparatus for depositing implants in soft tissue comprising:

a tubular member;

an introducer comprising an elongated tube adapted to contain a plurality of implants, said introducer having a distal end insertable into said soft tissue and a proximal end engaging said tubular member;

an obturator slidable within the introducer from said proximal end of said introducer; and an operating mechanism comprising a shuttle slidable within said tubular member, a trigger mechanism which reciprocally advances said shuttle forward within the tubular member upon each actuation of said trigger mechanism and retracts said shuttle rearward upon each release of said trigger mechanism, and a clutch coupling said obturator to said shuttle as said shuttle advances forward to eject an implant from said distal end of said introducer and decoupling said obturator from said shuttle as said shuttle retracts rearward.

54. The apparatus of claim 53 wherein said introducer has retaining means on said distal end retaining said implants within said introducer but permitting said implants to be pushed out of said distal end of said introducer by advancement of said obturator forward within said introducer.

55. The apparatus of claim 54 wherein said retaining means comprises at least one generally longitudinal slit in said distal end of said introducer forming a split end which is crimped.

56. The apparatus of claim 55 wherein said retaining means further comprises a double chamfer on said split end of said introducer forming a pair of pointed ends which are crimped.

* * * * *

UNITED STATES PATENT AND TRADEMARK OFFICE
CERTIFICATE OF CORRECTION

PATENT NO.     : 6,270,472 B1
DATED          : August 7, 2001
INVENTOR(S)    : James F. Antaki et al.

It is certified that error appears in the above-identified patent and that said Letters Patent is hereby corrected as shown below:

Column 3,
Line 43, "firer" should be -- further --.

Column 5,
Line 38, "by," should be -- by --.

Column 6,
Line 60, "lenti" should be -- Lenti --.

Column 8,
Line 40, "line 1" should be -- line 13s --.

Column 17,
Line 64, "walfing" should be -- walking --.

Signed and Sealed this

Seventh Day of May, 2002

*Attest:*

JAMES E. ROGAN
*Director of the United States Patent and Trademark Office*

*Attesting Officer*